United States Patent [19]

Chang et al.

[11] Patent Number: 5,192,330

[45] Date of Patent: Mar. 9, 1993

[54] ORTHOPEDIC DEVICE OF BIOCOMPATIBLE POLYMER WITH ORIENTED FIBER REINFORCEMENT

[75] Inventors: Fu-Kuo Chang, Palo Alto, Calif.; Kenneth Reifsnider, Blacksburg, Va.; James A. Davidson, Germantown, Tenn.; Frederick S. Georgette, Troy, Mich.

[73] Assignee: Smith & Nephew Richards, Inc., Memphis, Tenn.

[21] Appl. No.: 740,723

[22] Filed: Aug. 6, 1991

Related U.S. Application Data

[62] Division of Ser. No. 5,091, Jan. 20, 1987.

[51] Int. Cl.⁵ ............................................. A61F 2/32
[52] U.S. Cl. ........................................ 623/22; 623/18
[58] Field of Search ................. 623/16, 18, 22, 23, 623/66

[56] References Cited

U.S. PATENT DOCUMENTS

| | | |
|---|---|---|
| 3,660,199 | 5/1972 | Riccitiello et al. . |
| 3,707,006 | 12/1972 | Bokros et al. . |
| 3,893,196 | 7/1975 | Hochman ............................ 623/18 |
| 3,992,725 | 11/1976 | Homsy . |
| 4,065,340 | 12/1977 | Dickerson . |
| 4,164,794 | 8/1979 | Spector et al. . |
| 4,329,743 | 5/1982 | Alexander et al. . |
| 4,356,571 | 11/1982 | Esper et al. . |
| 4,459,708 | 7/1984 | Buttazzoni . |
| 4,534,919 | 8/1985 | McAliley et al. . |
| 4,535,487 | 8/1985 | Esper et al. . |
| 4,547,910 | 10/1985 | Roberts et al. . |
| 4,551,390 | 11/1985 | Canning et al. . |
| 4,604,097 | 8/1986 | Graves, Jr. et al. ................... 623/18 |
| 4,610,688 | 9/1986 | Silvestrini et al. . |
| 4,654,263 | 3/1987 | Cox . |
| 4,657,717 | 4/1987 | Cattanach et al. . |
| 4,662,887 | 5/1987 | Turner et al. . |
| 4,683,018 | 7/1987 | Sutcliffe et al. . |
| 4,713,426 | 12/1987 | Harris et al. . |
| 4,714,467 | 12/1987 | Lechner et al. ....................... 623/22 |
| 4,714,642 | 12/1987 | McAliley et al. . |
| 4,750,905 | 6/1988 | Koenemann ........................... 623/22 |
| 4,863,475 | 9/1989 | Andersen et al. ..................... 623/16 |
| 4,892,552 | 1/1990 | Ainsworth et al. .................... 623/16 |

FOREIGN PATENT DOCUMENTS

| | | |
|---|---|---|
| 0182580 | 5/1986 | European Pat. Off. . |
| 0246620 | 11/1987 | European Pat. Off. . |
| 3243861 | 3/1982 | Fed. Rep. of Germany . |
| 85/04323 | 10/1985 | PCT Int'l Appl. . |

OTHER PUBLICATIONS

Gohl, Walter et al., "Carbonfiber-Reinforced, Composite-Material for Endoprosthetics," pp. 1-78 (Apr. 1982).

Bradley, J. S. et al., "Carbon Fibre Reinforced Epoxy as a High Strength, Low Modulus Material for External Fixation Plates," *Biomaterials* vol. 1, pp. 38-40 (1979).

(List continued on next page.)

*Primary Examiner*—David J. Isabella
*Assistant Examiner*—Gina M. Gualtieri
*Attorney, Agent, or Firm*—Pravel, Gambrell, Hewitt, Kimball & Krieger

[57] ABSTRACT

Orthopedic device of biocompatible polymer with oriented fiber reinforcement. There is provided a device such as a hip stem which has a longitudinally curved body. The reinforcing fibers are continuous filament fiber plies with parallel orienated fibers in each ply. The plies are curved longitudinally to approximately correspond to the curve of the body. In one embodiment, there are longitudinally oriented fiber plies at or near the surfaces of the device and plies with fibers offset at 5°-40° from the longitudinal axis between the surface layers. The fiber orientation is balanced by providing a ply of negatively angled offset fibers of a similar angle for each positively angled offset ply. The device is made by molding plies preimpregnated with polymer (prepregs) simultaneously, by molding a plurality of prepregs into segments which are then molded together, or by molding a segment and incrementally molding additional layers of prepregs thereto in a series of progressively larger molds.

66 Claims, 8 Drawing Sheets

OTHER PUBLICATIONS

Fitzer, E. et al., "Torsional Strength of Carbon Fiber Reinforced Composites for the Application as Internal Bone Plates," *Carbon* vol. 18, pp. 383-387 (1979).

McKenna, G. B. et al., "Mechanical Properties of Some Fibre Reinforced Polymer Composites After Implantation as Fracture Fixation Plates," *Biomaterials* vol. 1, pp. 189-192 (1980).

McKenna, G. B. et al. "The Development of Composite Materials for Orthopedic Implant Devices," pp. 232-241 (Apr. 1976).

Forster, I. W. et al., "Biological Reaction to Carbon Fiber Implants: The Formation and Structure of a Carbon-Induced 'Neotendon'," pp. 299-307 (1977).

Tayton, Keith et al., "The use of Semi-Rigid Carbon-Fibre-Reinforced Plastic Plates for Fixation of Human Fractures," *Jnl of Bone and Joint Surgery*, vol. 64-B, pp. 105-111 (1982).

Musikant, S., "Quartz and Graphite Filament Reinforced Polymer Composites for Orthopedic Surgical Application," *Jnl Biomed. Mater. Res. Symposium*, vol. 1, pp. 225-235 (1971).

Hastings, G. W., "Carbon Fibre Composites for Orthopaedic Implants," *Composites*, pp. 193-197 (Jul. 1978).

Hunt, M. S., "Fibre Reinforced Composites for Orthopaedic Surgical Implants," *The South African Mechanical Engineer*, vol. 31, pp. 1-5 (Jan. 1981).

Bradley, J. S. et al., "Carbon Fibre-Reinforced Plastic for Orthopaedic Implants," *Mechanical Properties of Biomaterials*, Editors: Hastings & Williams, Ch. 30, pp. 379-386 (1980).

Scheer, Wolfgang, "Carbon Fiber Reinforced Epoxy Resin, a Material for Human Implants," pp. 251-277 (1981).

Soltesz, U. et al., "Investigation of Mechanical Behaviour of Fibre-Reinforced materials for Endoprosthetic Devices," *Biomaterials*, edited Winter et al., pp. 33-38 (1982).

Lipka, John M. et al., "The Role of Carbon Fibers in Orthopedic Implants: A Review," pp. 335-343 (date unknown); p. 336 not available.

Katz, J. Lawrence, "Present and Potential Biomedical Applications of Composite Materials Technology," pp. 452-476 (1984).

Fu-Kuo Chang et al., "Failure of Composite Laminates Containing Pin Loaded Holes Method of Solution," *Jnl of Composite Materials*, vol. 18, pp. 255-278 (May, 1984).

Fu-Kuo Chang, et al., "The Strengths of Fiber Reinforced Composite Bends," *Jnl of Composite Materials*, vol. 20, pp. 31-45 (Jan. 1986).

Gregory, M. A. et al., "Predicting Crack Growth Direction in Unidirectional Composites," *Jnl of Composite Materials*, vol. 20, pp. 67-85 (Jan. 1986).

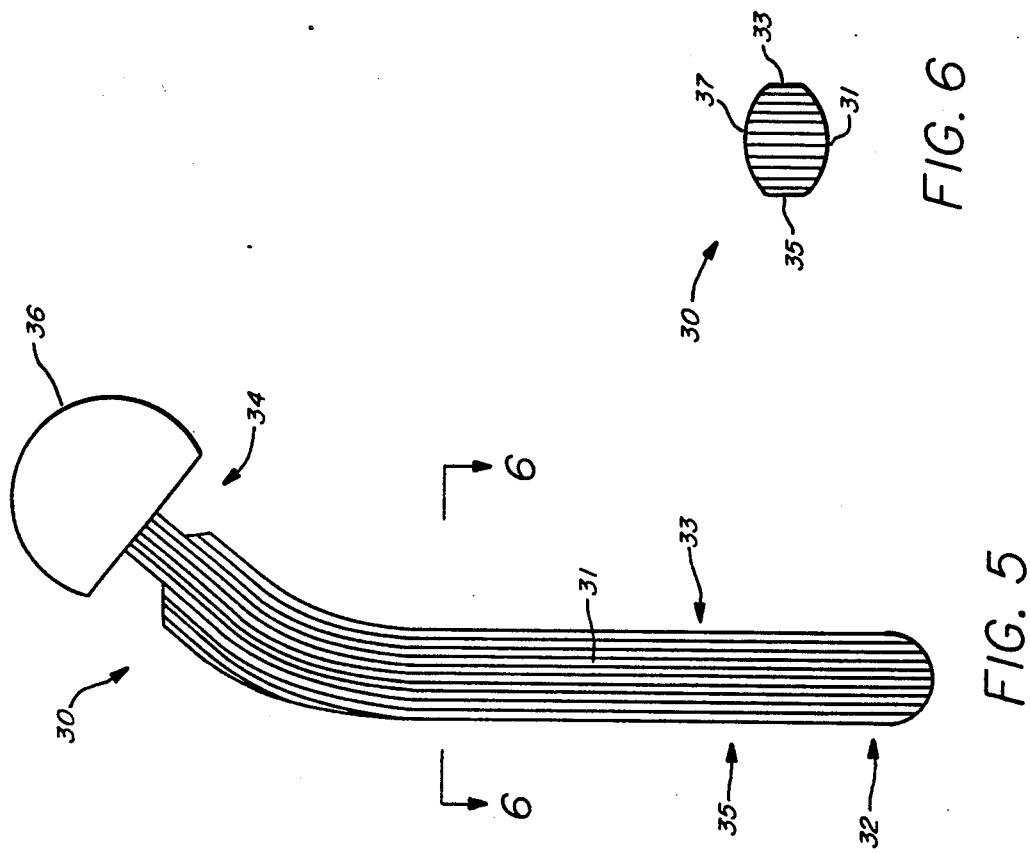
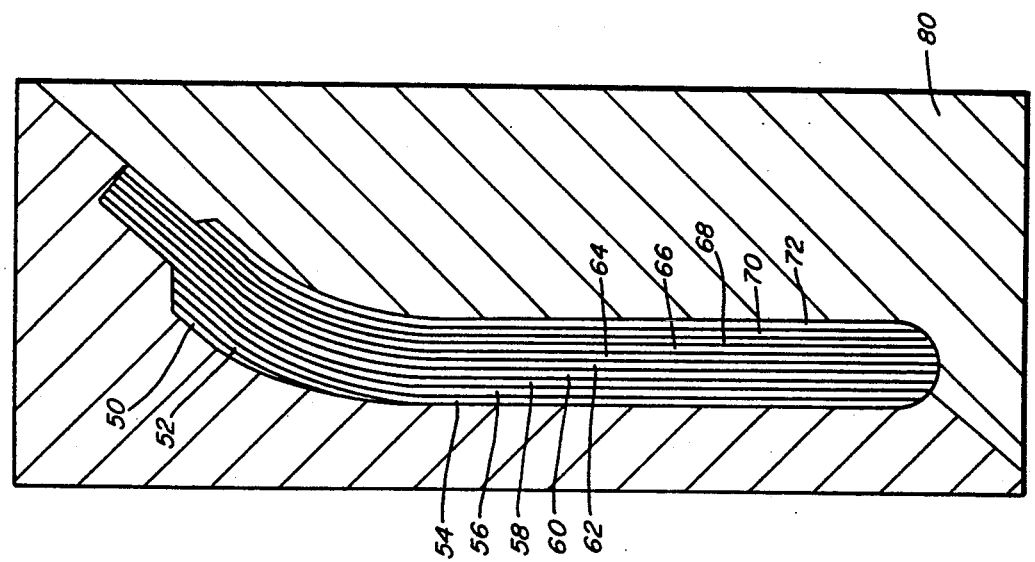

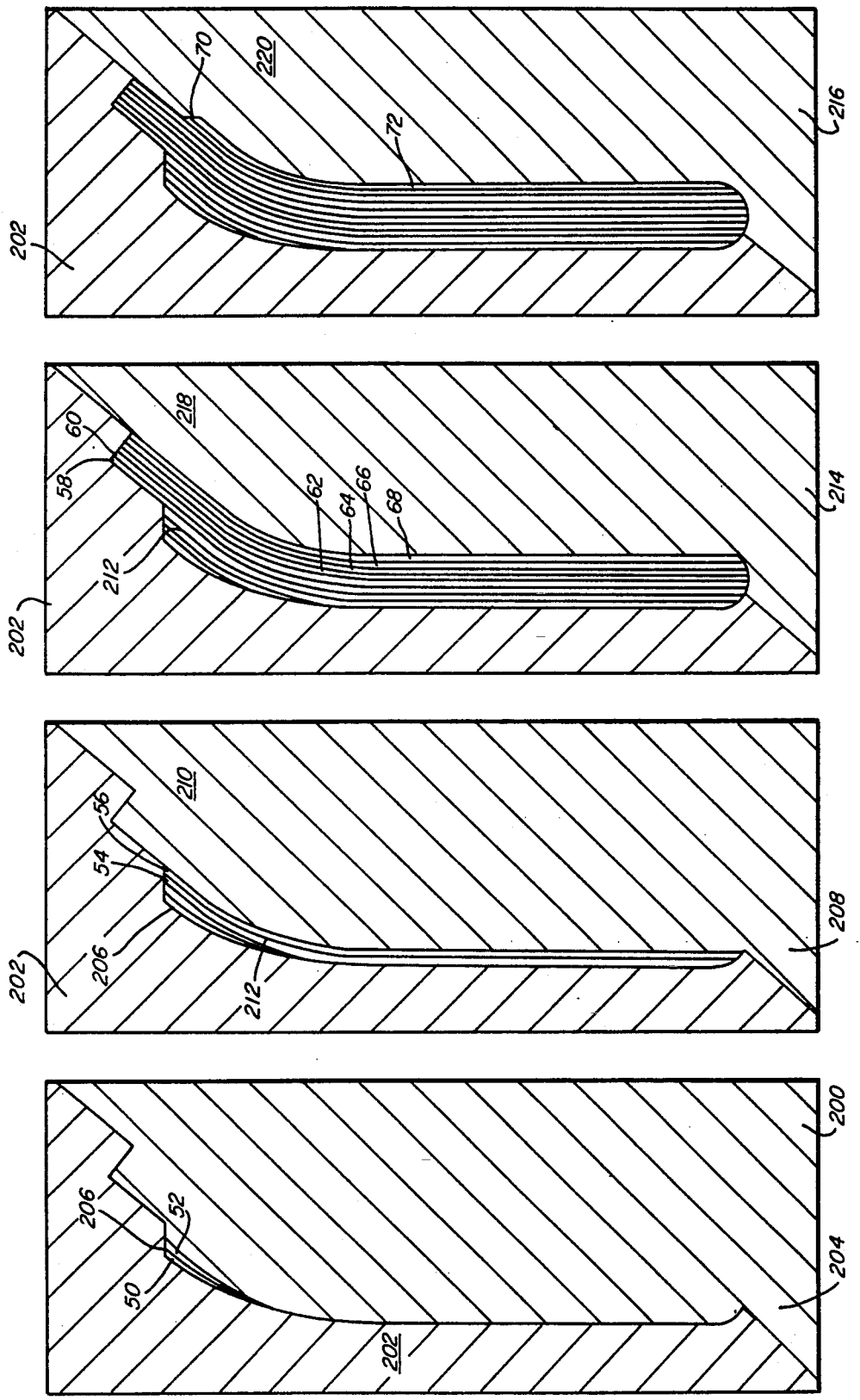

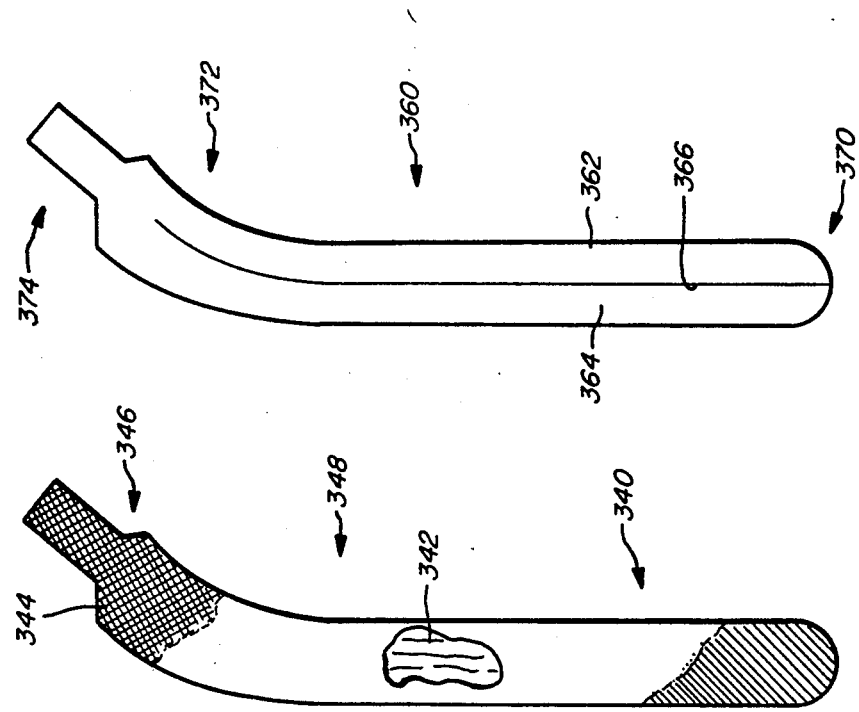
FIG. 18
FIG. 17
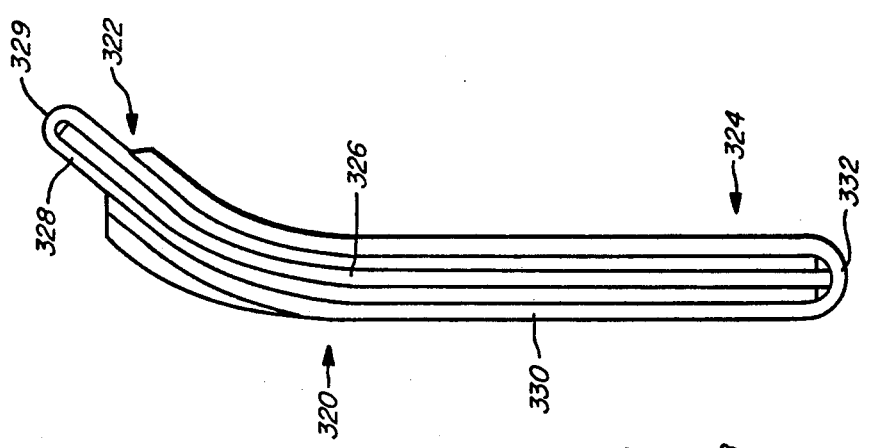
FIG. 16
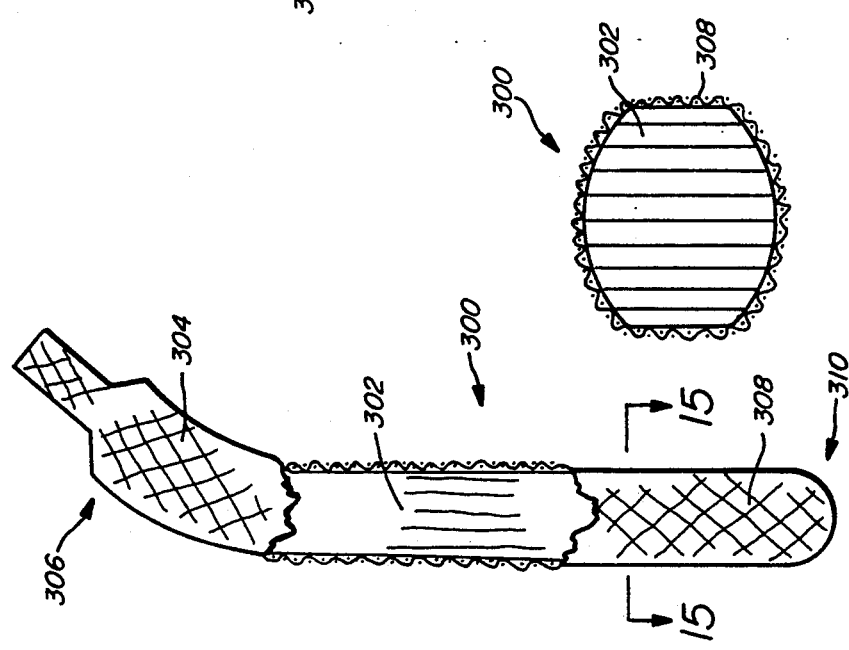
FIG. 15
FIG. 14

ORTHOPEDIC DEVICE OF BIOCOMPATIBLE POLYMER WITH ORIENTED FIBER REINFORCEMENT

RELATED APPLICATIONS

This application is a divisional of U.S. Ser. No. 005,091 filed Jan. 20, 1987.

1. Field of the Invention

This invention relates to load-bearing prosthetic devices for human implantation made of a fiber-reinforced biocompatible polymer matrix, and particularly to such devices in which the fibers are oriented to provide optimal load-bearing capabilities.

2. Background of the Invention

Composite materials are potentially well suited materials for the manufacture of prosthetic devices. In International Publication WO 85/04323, for example, composite materials were used to make orthopedic devices such as hip stems. The composite material comprised 30-70% of a biocompatible polymer matrix, such as polysulfone, reinforced with 70-30% continuous filament carbon fibers in the form of uniplanar sheets. In one version, the devices were made by stacking flat coupons to form blocks from which the devices were machined. In another version, patterned sheets were rolled upon themselves to form cylinders from which the device was fashioned.

It is an object of the present invention to provide a prosthetic device with an optimal fiber orientation which improves the load-bearing capability of the resulting prosthesis which, in use, is typically subject to complex cyclic loads.

SUMMARY OF THE INVENTION

The present invention provides a load-bearing prosthetic device for human implantation which has improved load-bearing properties. The prosthesis has a curved elongated body which includes a matrix of biocompatible polymeric material and a plurality of reinforcing fiber plies embedded within the matrix. The plies are curvilinearly disposed within the body in approximate correspondence with the curve thereof. The fibers are continuous and oriented parallel within each ply. Preferably, the device includes one or more plies in which the fibers are oriented along the longitudinal axis of the body of the prosthesis, and may also include one or more plies in which the fibers are oriented at an angle offset with respect to the longitudinal axis of the body. Most preferably, the fiber orientation of the various plies is arranged at such angles and in such an order to maximize the load-bearing and torque-bearing properties and durability of the device, while providing a low modulus. In this respect, the reinforcement may include both plies with fibers oriented parallel with the longitudinal axis of the body and plies with fibers offset at an angle substantially between ±5° and ±40° with respect to the longitudinal axis, with the longitudinally oriented fibers being disposed in the outermost layer of plies near the surfaces of the body and the number of offset plies being in the majority.

The present invention also provides a load-bearing prosthetic device for human implantation which includes a plurality of adjacent plies disposed within a biocompatible polymer matrix defining the shape of the device. The plies comprise continuous filament fibers oriented parallel within each ply. The fibers in at least one ply are oriented offset at a positive angle up to 90° with respect to a major axis of the device. For each such ply with a positive angle fiber orientation, there is essentially a ply with a substantially similar negative angle fiber orientation corresponding thereto. The device is thus provided with a substantially balanced reinforcing fiber orientation for improved load-bearing capability and torsion fatigue loading resistance.

The invention further provides a prosthetic device for human implantation with improved load-bearing capability and torsion fatigue loading resistance which has a curved elongated body including a matrix of biocompatible polymer and a plurality of reinforcing plies stacked parallel and adjacent to each other curvilinearly within the body in approximate correspondence with the curve thereof. The plies are formed of continuous filament fibers oriented parallel to each other within each ply. The device includes one or more plies with fibers oriented at a positive angle up to 90° with respect to the longitudinal axis of the body, preferably essentially between 5° and 40°, and essentially a ply with a substantially similar negative angle fiber orientation in approximately one-to-one correspondence with each ply having a positive angle fiber orientation. Preferably, at least one of the plies has fibers oriented parallel to the longitudinal axis of the body, especially in the plies at or near the surfaces of the body. Thus, the invention provides a balanced fiber orientation for maximum load-bearing and torque-bearing capabilities.

Still further, the invention provides a prosthetic device for human implantation with improved load-bearing capability and torsion fatigue loading resistance. The device includes a core made of a plurality of reinforcing fiber plies within a matrix of biocompatible polymer and a layer of continuous fibers overmolded in a biocompatible polymer matrix on the core. The plies are formed of a layer of continuous fibers oriented parallel to each other within each ply. The outer layer of overmolded continuous fiber may be a mantle which fits over at least an end of the core, a ply folded over at least an end of the core, or a winding of a continuous fiber around at least a part of the core.

BRIEF DESCRIPTION OF THE DRAWINGS

FIG. 4 is a sectional view of a mold used in a one-step molding process in which the fiber prepregs of FIG. 3 are formed into a hip stem according to the present invention.

FIG. 5 is a perspective view of a hip stem after removal from the mold of FIG. 4 and attachment of a stem roll head according to the present invention.

FIG. 6 is a cross-sectional view of the hip stem of FIG. 5 along the lines 6—6.

FIG. 10 is a sectional view of a mold in which medial prepregs seen in FIG. 3 are molded into a hip stem segment in the initial step of a multi-step hip stem fabrication process according to the present invention.

FIG. 11 is a sectional view of a mold in which additional medial prepregs seen in FIG. 3 and the segment molded in the mold of FIG. 10 are molded into a hip stem segment in the second step of a multi-step hip stem fabrication process according to the resent invention.

FIG. 12 is a sectional view of a mold in which lateral prepregs seen in FIG. 3 are molded into a hip stem segment with a premolded medial portion of a hip stem in an intermediate step of a multi-step hip stem fabrication process according to the present invention.

FIG. 13 is a sectional view of a mold in which lateral prepregs seen in FIG. 3 are molded with the premolded remainder of a hip stem in the final step of a multi-step hip stem fabrication process according to the present invention.

FIG. 14 is a perspective view, partly in cutaway, of a mantle-covered hip stem according to the present invention.

FIG. 15 is a sectional view of the hip stem of FIG. 14 as seen along the lines 15—15.

FIG. 16 is a sectional view of a hip stem with end-folded plies according to the present invention.

FIG. 17 is a perspective view, partly in cutaway, of a fiber-wound hip stem according to the present invention.

FIG. 18 is a perspective view of a distal-slotted hip stem according to the present invention.

DETAILED DESCRIPTION OF THE INVENTION

Figure 2:
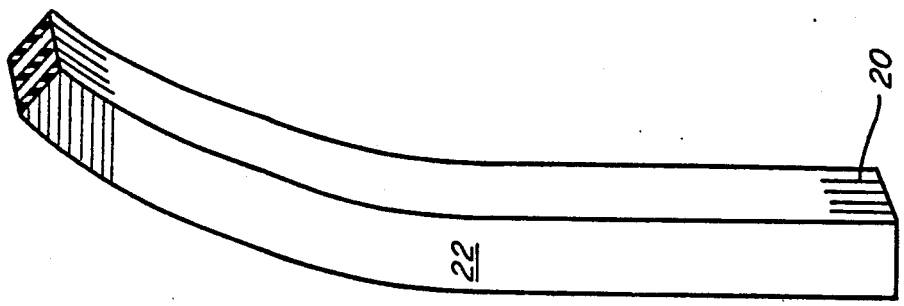
FIG. 2 is a perspective view of a longitudinally curved prosthesis reinforced with flat plies of continuous fibers.

The orthopedic device of the present invention includes a biocompatible polymer matrix reinforced with with high-strength fibers.

Biocompatible polymers suitable as the matrix material of the orthopedic implants of the present invention are well known. Specific representative examples include polysulfone, polyethersulfone, polyarylsulfone, polyphenylene sulfide, polycarbonate, aromatic polyamide, aromatic polyamideimide, thermoplastic polyimide, polyaryletherketone, polyetheretherketone, polyarylethernitrile, aromatic polyhydroxyether, thermosetting phenolics, medical grade epoxies and the like. In some applications it may be desirable to use a bioresorbable matrix polymer such as, for example, polylactate, D,L-lactide, polycaprolactone, polylactic acid, methylmethacrylate/N-vinylpyrrolidone copolymer, glycolic acid/lactic acid copolymer and the like. Of these contemplated matrix polymers, polysulfone and particularly polyethersulfone are preferred. For convenience, the biocompatible polymer matrix is referred to hereinbelow as polysulfone ("PS") with the understanding that other biocompatible polymers may also be employed as the matrix material in whole or in part in lieu thereof.

Suitable materials for the continuous filament fibers used in the present composite are generally biocompatible fibers well known for their reinforcing properties. Specific representative examples include carbon, glass, polyolefins such as polyethylene and polypropylene, polyetheretherketone, polyethylene terephthalate and the like. In some applications, it may also be desirable to use fibers made of bioresorbable materials such as those mentioned above, particularly when a bioresorbable matrix is employed. As examples of polyolefin fibers, the high strength polyolefin fibers described in U.S. Pat. No. 4,413,110 to Kavesh may be mentioned, but care must usually be taken when working with such fibers because their tensile properties may be adversely affected by exposure to a temperature above about 130° C. U.S. Pat. No. 4,413,110 is hereby incorporated herein by reference as though fully set forth. Preferably, carbon fibers are employed in the present invention. For convenience, the fibers are referred to hereinbelow as carbon fibers ("CF") with the understanding that other suitable fibers may also be employed as the reinforcement in lieu thereof or in combination therewith.

The CF fiber-reinforced PS polymer matrix of this invention generally conforms to a shape suitable for use as a prosthetic device. Typical of such devices are bone plates, tibial plates, hip stems and the like. For convenience, reference is made hereinbelow to hip stem prostheses for exemplary purposes with the understanding that the invention may be used with other load-bearing orthopedic devices.

For hip stems and other orthopedic devices having a curved elongated body, it has been discovered that the orientation of the fibers and the plies thereof can result in significant improvements in the load-bearing capabilities thereof not heretofore seen in such reinforced composite hip stems. In the present hip stem, the PS matrix defines the general shape of the body, and a plurality of reinforcing CF plies with a fiber orientation specified in more detail hereinbelow are embedded in the matrix for reinforcement.

Figure 1:
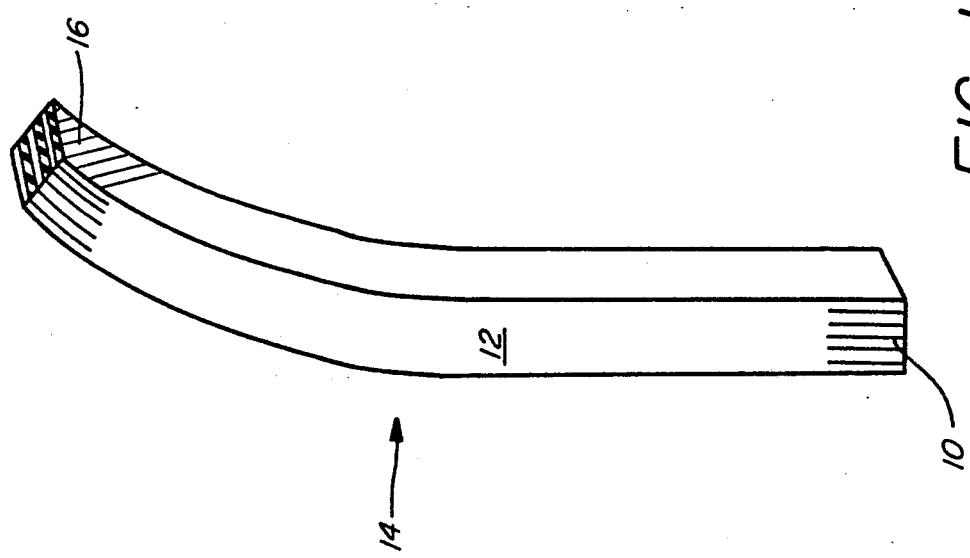
FIG. 1 is a perspective view of a longitudinally curved prosthesis reinforced with curvilinear plies of continuous fiber plies according to the present invention.

For optimum strength, the plies 10 are preferably curvilinearly disposed within the body 12 in approximate correspondence with the curve of the prosthesis 14, as seen in FIG. 1. As in International Publication WO 85/04323, the fibers 16 within each prepreg are continuous and parallel oriented. However, in contrast to the orientation obtained by stacking flat, planar sheets 20 into a block and machining into the body 22 seen in FIG. 2 and as described in International Publication WO 85/04323, the plies 10 in the present invention are preferably longitudinally curved or bent to correspond to the longitudinal curve or bend of the prosthetic device 14 and configured as if formed of stacked, curved sheets. The prosthesis of the present invention is thus preferably formed of composite bends rather than flat plates. It has been found that the optimum fiber orientation for longitudinally curved prepregs results in about a 40% increase in the load at failure in contrast to the optimum fiber configuration for stacked flat sheets.

Figure 3:
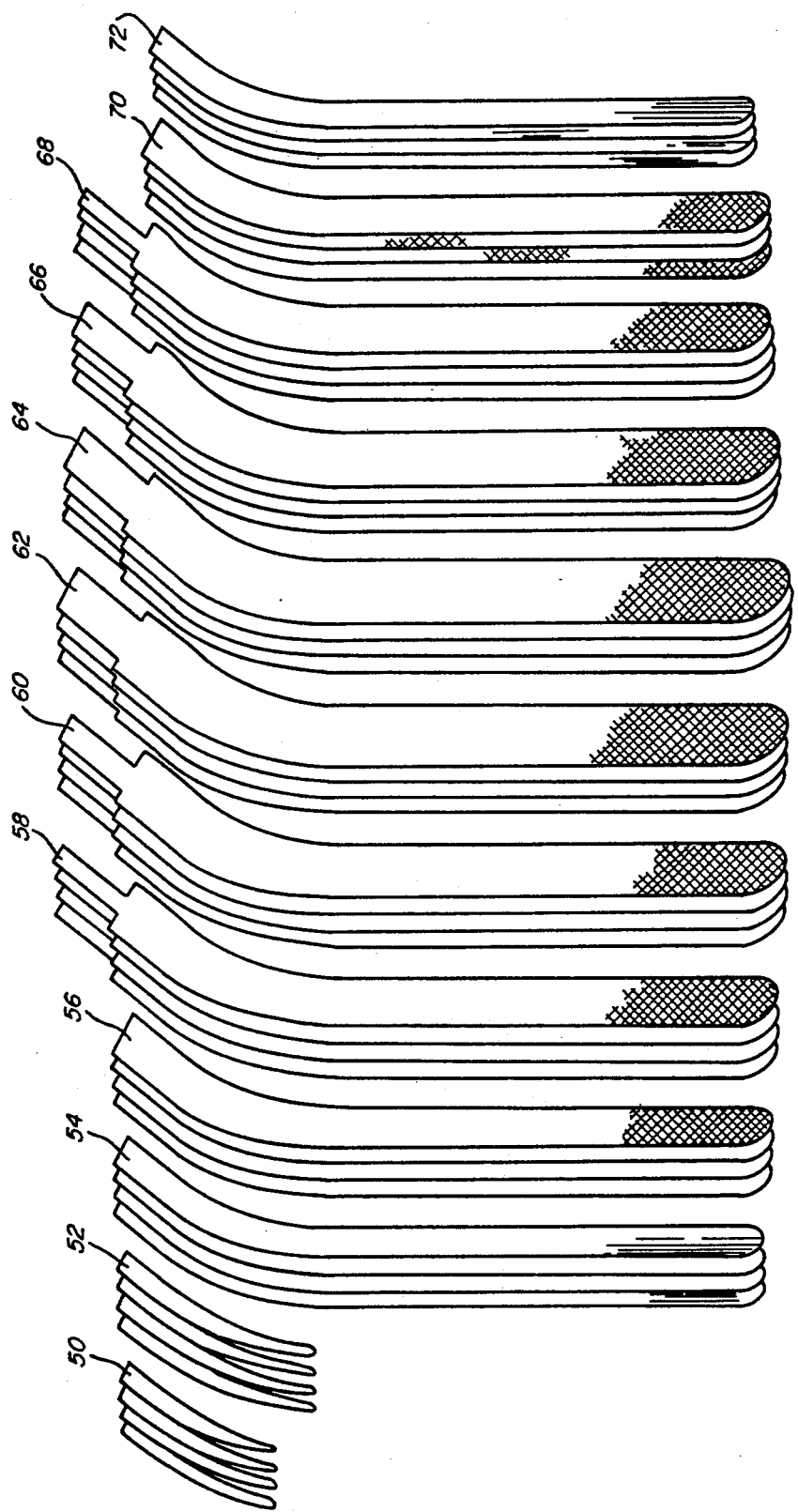
FIG. 3 is an exploded view of a fiber prepreg lay up for the manufacture of a hip stem prosthesis having composite bend, continuous fiber ply reinforcement with balanced orientation according to the present invention.

As seen in the lay up of FIG. 3, the fibers in each ply 50-72 are continuous and parallel. The plies 50-72 should include one or more, and preferably a multiplicity of plies 54 and 72 having fibers oriented along the longitudinal or major axis of the body. It has been found that this configuration is preferred to optimize the load-bearing and torque-bearing capabilities of the resulting prosthesis. Further, if the longitudinally oriented fiber plies 54 and 72 are used with offset or angled oriented fiber plies 56-70, the longitudinally oriented fiber plies 54 and 70 are preferably disposed near an outer surface of the stack of reinforcing fiber plies as shown in FIG. 3. The load-bearing and torque-bearing capabilities of the resulting prosthesis are improved when such longitudinally oriented fiber plies 54 and 70 are disposed in the outer layers of the plies 50-72 near the surface of the prosthesis.

It has also been found that the load-bearing and torque-bearing capabilities of the resulting prosthesis are improved when there are included plies 52-70 with fibers offset from the longitudinal or major axis of the device. The angle of orientation may be up to 90° with respect to the longitudinal axis, but for optimum reinforcement, the offset fiber plies should be substantially between 5° and 40° inclusive with respect to the longitudinal axis of the hip stem. For example, the fiber orientation of the plies 54-72 is shown as 0° for plies 54 and 72, ±7.5° for plies 56 and 70, ±15° for plies 58 and 68, ±22.5° for plies 60 and 66, and ±30° for plies 62 and 64.

It has further been found that the reinforcement is improved by providing a balanced fiber orientation. By the term "balanced" is meant that for each ply of fibers offset at a positive angle with respect to the longitudinal axis there is essentially a corresponding ply with fibers offset at about the same, but negative angle with respect to the longitudinal axis of the hip stem. Quite surprisingly, including more plies offset toward an off-axis load (positive angle orientation) than away from the off-axis load (negative angle orientation), which would be expected to improve the load-bearing capability, generally detracts therefrom. An unbalanced fiber orientation generally results in poorer reinforcement and ultimate load-bearing and torque-bearing capabilities than the balanced orientation. As used herein, the designation "±" connotes a ply of positive offset and a ply of negative offset, unless the context indicates the conventional meaning "plus or minus".

As used herein, the term "prepreg" refers to a sheet, layer or ply of continuous filament fibers oriented parallel to each other within the prepreg and which, prior to molding, are pre-coated or pre-impregnated with matrix polymer. The prepregs employed for reinforcement within the PS matrix are generally known in the art and may be prepared, for example, according to the procedure described in International Publication WO 85/04323 which is hereby incorporated herein by reference to the extent necessary to describe the preparation of CF prepregs to be used as reinforcement in a PS matrix. Briefly, a CF tow, typically comprising bundles of filaments having 3,000-15,000 filaments/bundle, are passed through a PS solution, such as PS in methylene chloride, and coated with the PS solution. The coated fibers are then wound spirally on a drum in a single layer and dried to form the prepreg. For use in the present invention, the prepreg may be formed with the desired fiber orientation, shape and geometry by using a drum with a surface corresponding to the desired geometry, e.g. flat or curved, and by cutting to shape. Alternatively, flat prepregs may be preshaped by making the prepreg flexible or malleable, e.g. by heat or solvent, and working or molding the prepreg into the desired shape.

Referring to FIGS. 5 and 6, a typical hip stem 30 generally has a tapered stem portion 32 which in use is inserted in a cavity formed in cortical bone in the upper portion of the femur, and a neck portion 34 angled with respect to the stem portion 32, to the end of which a stem roll head 36 is attached, e.g. by press-fitting or the use of adhesive, or made integral therewith. The hip stem 30 also has an anterior surface 31, a posterior surface 37 opposite thereto, a lateral surface 33, and a medial surface 35. As described in more detail hereinbelow, prepregs having a radius of curvature approximately corresponding with the angle between the neck and stem portions of the device are stacked and molded to form a bent beam of generally rectangular or elliptical cross-section from which the final prosthesis is formed. Alternatively, sequential layers, each comprising a plurality of stacked curved prepregs are molded with matched radii of curvature, and the sequential layers molded into the final form; or an initial segment of the prosthesis is molded from stacked fiber prepregs, and additional layers of fiber prepregs are molded onto a surface of the segment in a series of molding steps to obtain the prosthesis.

The prosthesis of the present invention may be fabricated by placing the flexible or malleable prepregs, or precurved or prebent prepregs in the desired configuration and molding the polymer matrix thereover in a single-molding operation as generally shown in FIGS. 3-6. Precurved prepregs 50-72 are positioned in mold 80 in the stacked configuration shown in FIGS. 3 and 4 to obtain the desired fiber orientation. The length and width of the hip stem is controlled by the length and width of each prepreg 50-72 in the stack, and the thickness by the thickness and number of prepregs 50-72. The length and width of adjacent prepregs 50-72 in the stack is gradually increased from the medial prepregs 50 and the lateral prepregs 72 toward the centrally disposed prepregs 62 and 64. The stacked prepregs 50-72 are then molded together by compression molding in mold 80 at a suitable elevated temperature and pressure, and the hip stem 30 is machined, ground, polished and/or otherwise surface finished or treated to obtain the geometry and finish as desired.

Figure 9:
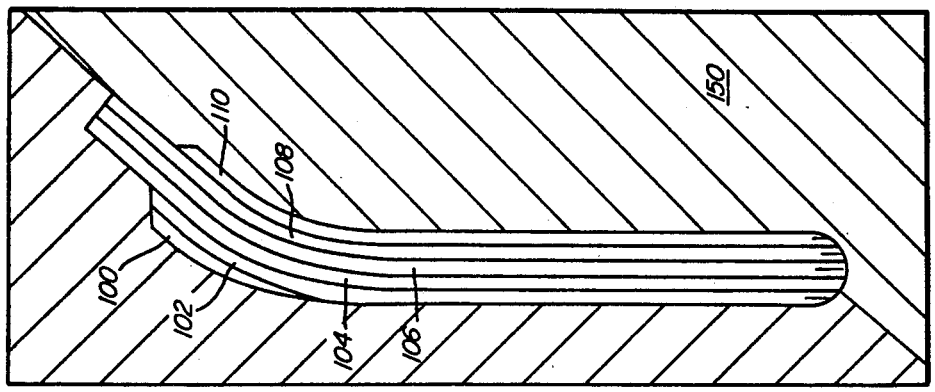
FIG. 9 is a sectional view of a mold in which the hip stem segments of FIG. 8 are placed according to the present invention.
Figure 8:
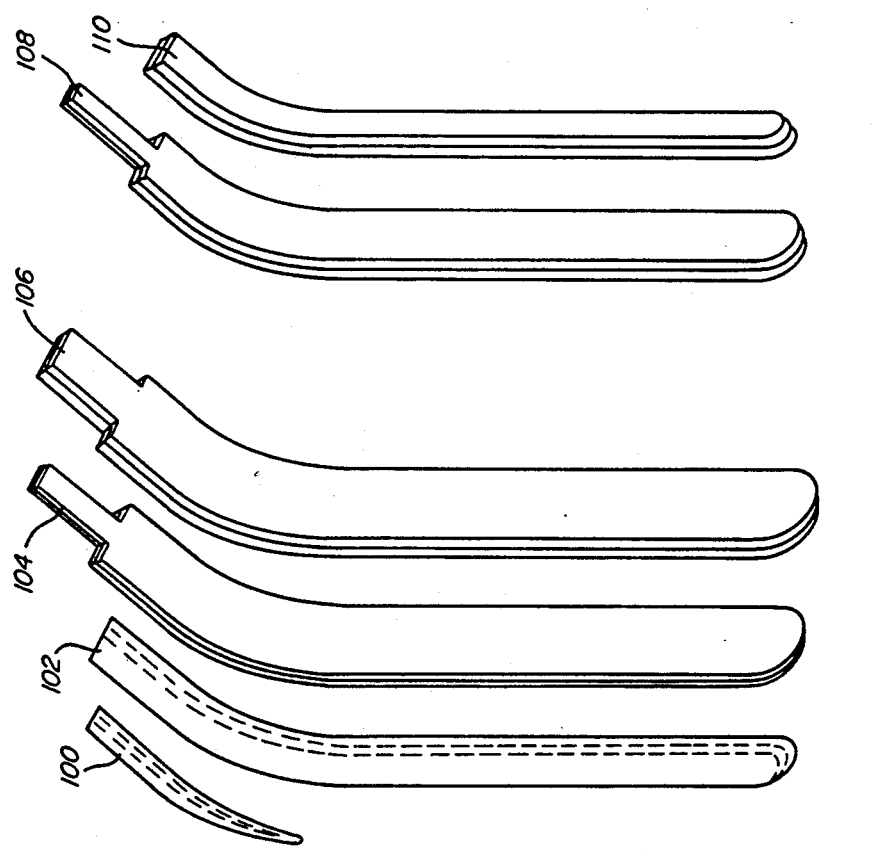
FIG. 8 is an exploded view of a segment lay up used in the manufacture of a hip stem in a two-step molding process according to the present invention.
Figure 7:
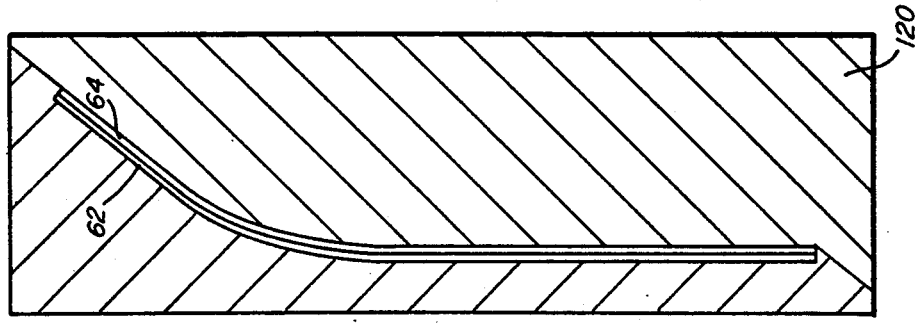
FIG. 7 is a sectional view of a mold used to make a hip stem segment from the prepregs seen in FIG. 3 according to the present invention.

To better assure that the desired fiber orientation is obtained, the prepregs 50-72 may be molded into segments 100-112 of varying curvature as seen in FIG. 8. For example, in the fabrication of hip stem 30, the segments 100-112 are prepared from stacked prepregs. Longitudinally oriented prepregs 62 and 64, for example, are stacked and compression molded in mold 120 as shown in FIG. 7 at a suitable temperature and pressure to form the segment 106. Prepregs 50 and 52, 54 and 56, 58 and 60, 66 and 68, and 70 and 72 are similarly compression molded to form the segments 100, 102, 104, 108 and 110, respectively. The inside radius of curvature of segment 100 matches the outside radius of curvature of segment 102. Similarly, the segments 104-110 are prepared with sequentially matched radii of curvature. The segments 100-110 are then compression molded together in mold 150 in FIG. 9 at a suitable elevated temperature and pressure to form the hip stem 30. As in the single-step method, the size and fiber orientation of the prepregs 50-72 in each segment 100-110 is prearranged as desired.

In still another embodiment, a plurality of longitudinally curved or curvable prepregs 50 and 52 are compression molded in mold 200 having an outer form 202 and inner form 204 as seen in FIG. 10. The resulting body 206 from the mold 200 in FIG. 10 thus resembles the segment 100 in FIGS. 8 and 9. The body 206 is then placed in mold 208 with a different inner form 210 but the same outer form 202. Additional prepregs 54 and 56 are then layered on top of the body 206 and compression molded to obtain the body 212. Additional layers of prepregs with the desired fiber orientation are sequentially molded onto the body 212 in a series of molds such as molds 214 and 216 with new inner forms 218 and 220, respectively, to obtain the hip stem 30. Instead of using entirely different molds in each step of the molding process, the outer form 202 may be left in contact with the respective body as the inner form of the mold is sequentially replaced with one having an incrementally larger form. It is readily appreciated that the sequential molds 200, 208, 214 and 216 may also begin with the molding of the lateral layer of prepregs 70 and 72 and progress by sequentially molding prepregs 68 down through 50 to the medial face of the body, or begin with the middle layer and sequentially mold additional layers of prepregs to either face thereof.

Numerous benefits are obtained with the foregoing methods of hip stem fabrication. Primarily, the use of prepregs formed into longitudinally curved bends substantially enhances the load capability of the resulting hip stem. In addition, the fibers may be properly oriented in an order which also enhances loading capability. The risk that an improper orientation or order may result is substantially eliminated. This is in contrast to the method in which prepregs are stacked flat and molded to form a block from which the hip stem is then machined. In the latter method, there is a risk that the block may be rotated or turned out of the proper orientation or alignment for optimum strength, or that the order of the oriented fiber sheets largely determined by the position of the machine cut at the surface of the prosthesis may adversely affect the ultimate strength of the hip stem. However, in the present method, particularly with the segmented layer ("two-step") molding and the incremental layer ("multi-step") molding methods, the proper ordering of the prepreg fiber orientations can be carefully controlled.

In another embodiment, a sheath or layer of continuous fibers is placed at or near the surface of the prosthetic device in a plane parallel to such surface, particularly at the neck and distal end regions of the hip stem. The surface layer or sheath primarily provides a substantial reduction in the tendency for damage by cyclic torsional loading. However, there is also some tendency for the plies to delaminate at opposed adjacent faces along the longitudinal axis, under cyclic loading conditions. This is particularly true when curved plies are used instead of flat plies. Thus, while the failure load may be greater using curved prepregs instead of flat prepregs, the curved prepregs may result in an earlier failure because of their relatively greater tendency to delaminate when subjected to cyclic loading. The sheath further serves to inhibit this delamination tendency.

The sheath of continuous fiber may be provided in different ways. For example, the sheath may be provided in the form of a mantle or sock of fibers which fits over the molded prepregs as seen in FIGS. 14 and 15; by folding a prepreg or layer thereof over at an end of the hip stem as seen in FIG. 16; or in the form of a fiber winding around the molded prepregs as seen in FIG. 17.

In FIGS. 14 and 15, the hip stem 300 has a core 302, a mantle 304 covering the neck 306, and a mantle 308 covering the distal end 310. The mantles 304 and 308 are made of woven or braided fibers and shaped to correspond with the shape of the respective portions 306 and 310 of the core 302 over which they fit snugly. The core 302 is made of premolded prepregs which may be either in a stacked plate or curved bend configuration. The mantles 304 and 308 preferably comprise fibers oriented in two or more general directions for optimum reinforcement, e.g. $\pm 30°$ to $\pm 60°$ from longitudinal. The hip stem 300 is fabricated by first molding the core 302, positioning the mantles 304 and 308 in place, and overmolding the mantles 304 and 308 onto the core 302. The mantles 304 and 308 may, if desired, be pre-impregnated with PS prior to the overmolding.

In FIG. 16, the hip stem 320 has a neck 322 and a distal end 324, and is generally made of molded prepreg segments 326. The prepreg segment 328 adjacent the surface at the neck 322 is roughly twice as long as other segments 326 extending into the neck 322 and is folded over the neck 322 in a U shape to cover the terminal ends of the segments 326 at neck 322 with a layer of continuous fibers 329. Similarly, the prepreg segment 330 adjacent the surface at the distal end 324 is folded thereover in a U shape to cover the terminal ends of the segments 326 and 328 at the distal end 324 to form a layer of continuous fibers 332. In this embodiment, the continuous fiber layers 329 and 332 will have the parallel fiber orientation of the longer prepregs used in the respective segments 328 and 330 which preferably include fibers oriented in longitudinal and offset directions as described above.

The segments 328 and 330 may be bent or folded by premolding each into a U shape of predetermined dimension and overmolded in a subsequent molding step over the premolded segments 326. Alternatively, the prepregs may be rendered pliable, e.g. by heating or solvents, folded or bent into shape to fit over the premolded segments 326 and then molded thereto. While the end-folded prepregs 328 and 330 have been illustrated with reference to a longitudinally curved prepreg construction, a similar end-folded configuration can be employed with the flat plate hip stem construction.

In FIG. 17, the hip stem 340 has a premolded core 342 made of stacked curved or flat prepregs as described above and a layer of continuous wound fibers 344 thereover. While it is not always necessary to have the fiber layer 344 over the entire surface of the core 342, it is desirable to have the fiber layer 344 at the neck 346 and mid-stem region 348. The fibers in the layer 344 are preferably helically wound on the stem 340 in several plies offset from the longitudinal axis in at least two directions, for example from about $\pm 30°$ to about $\pm 60°$.

In FIG. 18, another embodiment is shown for minimizing the tendency for delamination by shear. The hip stem 360 is made of lateral prepregs or segments 362 and medial prepregs or segments 364. A centrally disposed longitudinal slot 366 is formed between adjacent central prepregs extending from the distal end 370 up to the mid-stem region 372. The slot 366 should not extend into the neck region 374. The adjacent prepregs 362 and 364 on either side of the slot 370 are not laminated together along the length thereof. This inhibits the development of delaminating shear forces, and hence substantially prevents fracture by such forces. The slot 366 may be readily formed during molding of the stem 360 by including in the above-described molding process a sheet or layer of a material which does not mold with or adhere to the matrix polymer employed, such as polyethylene in the case of the PS matrix. The non-molding sheet or layer may be left in place following molding, or be removed as desired.

EXAMPLES

Figure 20:
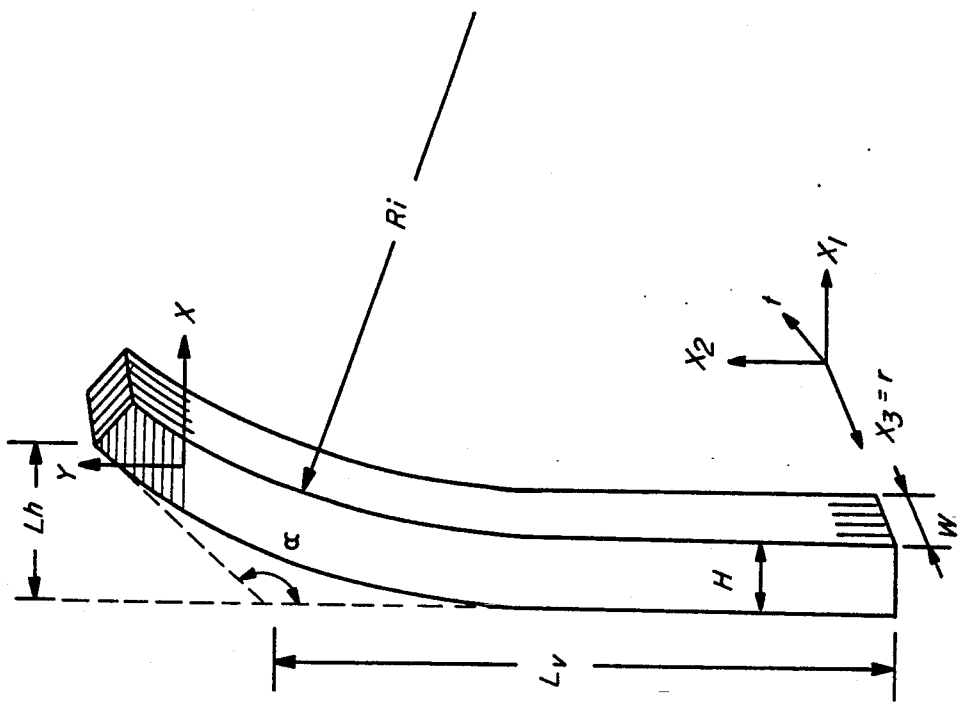
FIG. 20 illustrates a geometrical configuration of a flat plate reinforced beam used as a model for numerically calculating load at failure for various fiber orientations.
Figure 19:
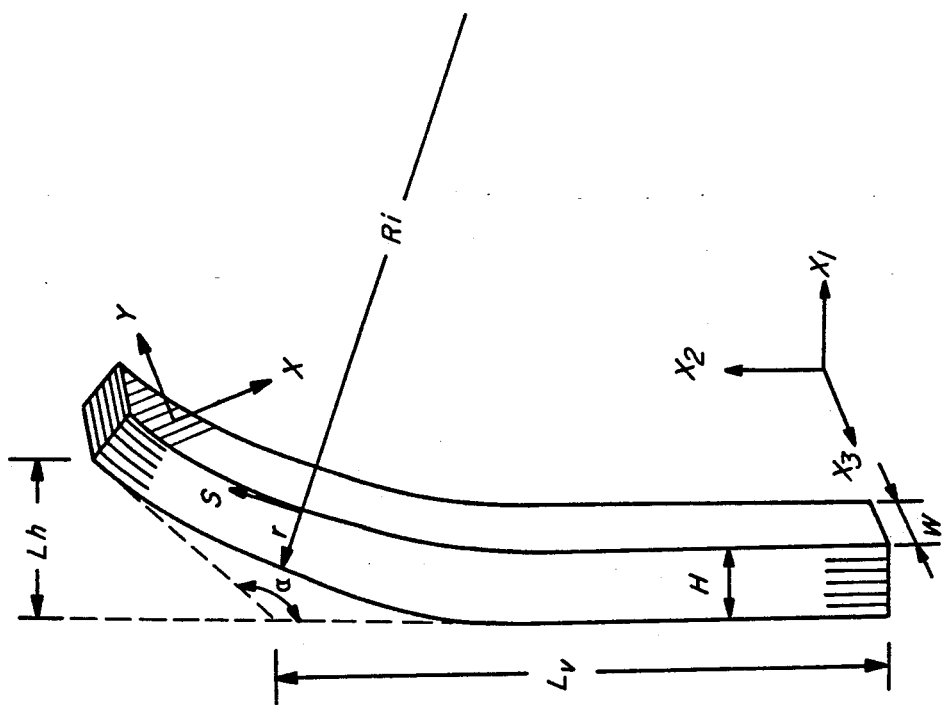
FIG. 19 illustrates a geometrical configuration of a composite bend reinforced beam used as a model for numerically calculating load at failure for various fiber orientations.
Figures 21, 22:
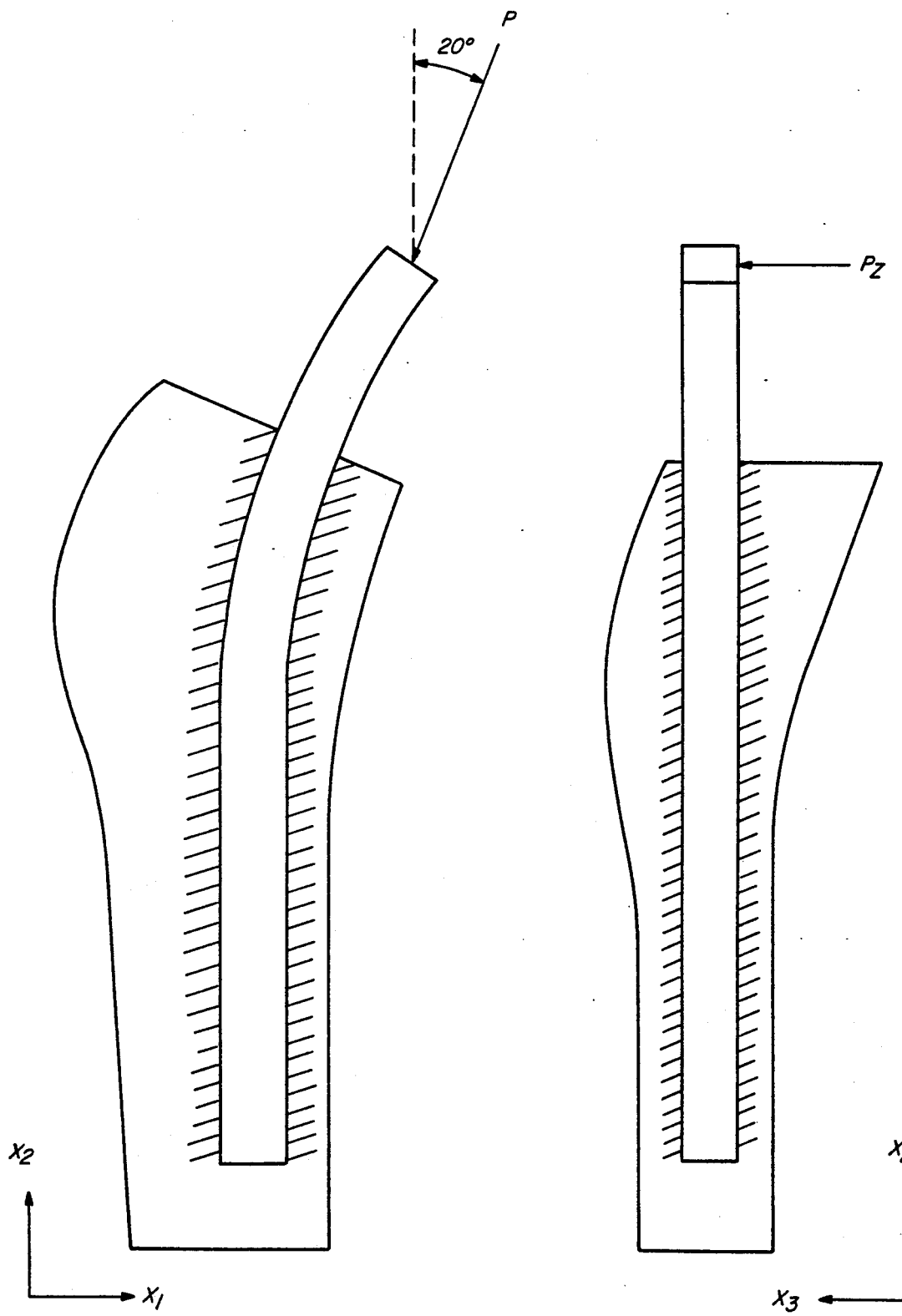
FIG. 21 illustrates an anterior view of loading conditions used for numerically calculating load at failure for the beams of FIGS. 19 and 20.
FIG. 22 illustrates a lateral view of the loading conditions seen in FIG. 21.

To demonstrate the effect on failure load of prepreg geometry (composite curved bends v. stacked plates) and balancing orientations, numerical finite element analysis was employed using the curved beam models seen in FIGS. 19 and 20 under the loading conditions shown in FIGS. 21 and 22 as a model to approximate a hip stem. With reference to the geometric dimensions and angles shown in FIGS. 19 and 20, the dimensions used for the numerical analysis are listed in Table I. Material properties used for the calculations were based on a polysulfone matrix and carbon fiber reinforcement and are listed in Table II. For the off-axis load $P_z$ shown in FIG. 22, it was assumed that $P_z$ was 20 percent of the axial load P shown in FIG. 21. The results of various fiber orientations and prepreg geometries are presented in Table III.

TABLE I

| | |
|---|---|
| H = | 0.51 inches |
| W = | 0.57 inches |
| $R_i$ = | 5.8 inches |
| $a$ = | 136 |
| $L_v$ = | 5.4 inches |
| $L_h$ = | 2.6 inches |

TABLE II

| Property | Magnitude |
|---|---|
| Longitudinal Tensile Modulus | $E_x = 1.9 \times 10^7$ psi |
| Transverse Tensile Modulus | $E_y = 1.2 \times 10^6$ psi |
| Shear Modulus | $E_{yz} = 1.0 \times 10^6$ psi |
| Poisson's Ratio | $\nu_{xy} = 0.35$ |
| Poisson's Ratio | $\nu_{yz} = 0.35$ |
| Longitudinal Tensile Strength | $X_T = 2.15 \times 10^5$ psi |
| Longitudinal Compressive Strength | $X_c = 1.3 \times 10^5$ psi |
| Transverse Tensile Strength | $Y_T = 5 \times 10^3$ psi |
| Transverse Compressive Strength | $Y_c = 1.5 \times 10^4$ psi |
| Play Shear Strength | $S = 1.4 \times 10^4$ psi |

TABLE III

| Ex. No. | Ply Geometry | Ply Fiber Orientation | Balancing | Initial Failure Load |
|---|---|---|---|---|
| 1 | LCB[1] | $[0_2/\pm5/\pm10/\pm15/\pm20]_s$ | Balanced | 3131 lbs |
| 2 | LCB | $[0_2/\pm7.5/\pm15/\pm22.5/\pm30]_s$ | Balanced | 3325 lbs |
| 3 | LCB | $[0_2/\pm10/\pm20/\pm30/\pm40]_s$ | Balanced | 3167 lbs |
| 4 | LCB | $[0_2/\pm11.25/\pm22.5/\pm33.75/\pm45]_s$ | Balanced | 3137 lbs |
| 5 | LCB | $[0_2/\pm30/\pm45/\pm60/90_2]_s$ | Balanced | 2688 lbs |
| 6 | LCB | $[0_2/\pm15/\pm30/\pm45/90_2]_s$ | Balanced | 2955 lbs |
| 7 | LCB | $[0_2/(\pm20)_4]_s$ | Balanced | 3244 lbs |
| 8 | LCB | $[0_2/(\pm30)_4]_s$ | Balanced | 3149 lbs |
| 9 | LCB | $[0_2/\pm10/\pm20/\pm30/\pm30]_s$ | Balanced | 3198 lbs |
| 10 | LCB | $[0_2/\pm20/\pm30/\pm20/\pm30]_s$ | Balanced | 3225 lbs |
| 11 | LCB | $[0_2/\pm30/\pm60/\pm30/\pm60]_s$ | Balanced | 2827 lbs |
| 12 | LCB | $[(\pm30)_5]_s$ | Balanced | 2272 lbs |
| 13 | LCB | $[(\pm45)_5]_s$ | Balanced | 1296 lbs |
| 14 | LCB | $[\pm30/\pm60/\pm45/0_2/\pm30]_s$ | Balanced | 1976 lbs |
| 15 | LCB | $[(0/90)_5]_s$ | Balanced | 2247 lbs |
| 16 | LCB | $[0_{10}]_s$ | Balanced | 2969 lbs |
| 17 | LCB | $[0_2/\pm30/0/\pm45/0/\pm30]_s$ | Balanced | 3042 lbs |
| 18 | LCB | $[0_2/\pm30/90/0_2/\pm30/90]_s$ | Balanced | 2956 lbs |
| 19 | LCB | $[0_2/\pm45/90/0_2/\pm45/90]_s$ | Balanced | 2760 lbs |
| 20 | LCB | $[0_2/\pm45/90/0_2/\pm60/90]_s$ | Balanced | 2750 lbs |
| 21 | LCB | $[0_2/\pm30/0_2/\pm30/0_2]_s$ | Balanced | 3197 lbs |
| 22 | LCB | $[0_2/\pm45/0_2/\pm45/0_2]_s$ | Balanced | 3030 lbs |
| 23 | LCB | $[0_2/90_2/\pm30/\pm45/\pm60]_s$ | Balanced | 2465 lbs |
| 24 | LCB | $[0/10/20/30/40/50/60/70/80]_s$ | Unbalanced | 1999 lbs |
| 25 | LCB | $[0_2/30_2/45_2/30_2/90_2]_s$ | Unbalanced | 2138 lbs |
| 26 | LCB | $[0_2/30/45/30/45/30/45/30/45]_s$ | Unbalanced | 2130 lbs |
| 27 | LCB | $[0/10/0/20/0/30/0/40/0/50]_s$ | Unbalanced | 2596 lbs |
| 28 | LCB | $[0/30/45/60(90)_2]_s$ | Unbalanced | 1911 lbs |
| 29 | LCB | $[(0/45)_5]_s$ | Unbalanced | 2300 lbs |
| 30 | LCB | $[0_2/30_2/45_2/60_2/90_2]_s$ | Unbalanced | 2100 lbs |
| 31 | LCB | $[0/45/0/30/0/60/0/90/0/90]_s$ | Unbalanced | 2322 lbs |
| 32 | LCB | $[0/10_2/20_2/30_2/40_2/90]_s$ | Unbalanced | 2173 lbs |
| 33 | LCB | $[0_2/\pm7.5/\pm15/\pm22.5/\pm30]_s$ | Unbalanced | 3325 lbs |
| 34 | LCB | $[0_2/\pm7.5/\pm15/\pm22.5/\pm30_2]_s$ | Unbalanced | 3185 lbs |
| 35 | LCB | $[0_2/\pm7.5/\pm15/22.5_2/\pm30]_s$ | Unbalanced | 3325 lbs |
| 36 | LCB | $[0_2/\pm7.5/15_2/\pm22.5/\pm30]_s$ | Unbalanced | 3313 lbs |
| 37 | FP[2] | $[0/0/0/45/25]_s$ | Unbalanced | 1418 lbs |
| 38 | FP | $[0/0/0/\pm15]_s$ | Balanced | 1016 lbs |
| 39 | FP | $[0/\pm10/\pm20]_s$ | Balanced | 1197 lbs |
| 40 | FP | $[0/\pm15/\pm30]_s$ | Balanced | 1386 lbs |
| 41 | FP | $[0_5]_s$ | Balanced | 990 lbs |
| 42 | FP | $[0_2/\pm45/0]_s$ | Balanced | 1436 lbs |
| 43 | FP | $[0/90/0/90/0]_s$ | Balanced | 1408 lbs |
| 44 | FP | $[45/30/60/0]_s$ | Unbalanced | 2332 lbs |
| 45 | FP | $[45/30/60/60]_s$ | Unbalanced | 1744 lbs |
| 46 | FP | $[45/45/60/0]_s$ | Unbalanced | 1564 lbs |
| 47 | FP | $[45/30/60/0/]_s$ | Unbalanced | 2545 lbs |
| 48 | FP | $[60/30/60/0]_s$ | Unbalanced | 1846 lbs |
| 49 | FP | $[45/30/60/0]_s$ | Unbalanced | 2332 lbs |
| 50 | FP | $[0/45/30/60]_s$ | Unbalanced | 1666 lbs |
| 51 | FP | $[60/30/45/0]_s$ | Unbalanced | 1233 lbs |

TABLE III-continued

| Ex. No. | Ply Geometry | Ply Fiber Orientation | Balancing | Initial Failure Load |
|---|---|---|---|---|
| 52 | FP | [30/45/60/0]$_s$ | Unbalanced | 2283 lbs |
| 53 | FP | [60/30/0/45]$_s$ | Unbalanced | 1240 lbs |

Notes for Table III:
[1]"LCB" = longitudinally curved bends (see FIG. 19).
[2]"FP" = flat plates (see FIG. 20).
[3]Fiber orientations are given in degrees and ordered from an exterior surface for each layer into the middle plane, symmetric about the middle plane as indicated by the "s" subscript; "±" indicates one layer at a positive angle and one at a negative angle.

Examples 1–23 show that in order to achieve optimal strength the plies on the outer surfaces should contain fibers longitudinally oriented (0 degrees), and the maximum offset of the fiber orientations should be about ±40° or less. The optimal fiber orientations are seen in Examples 2, 7 and 10. From this, similar fiber orientations such as [0/±10/(0/±15)/(±15)/(±22.5)/(±30)]$_s$ and [0/(±10)/(±20/±30/±20/±30)] can also be considered equivalents to the optimum ply orientations listed in Table III.

Examples 24–32 show that completely unbalanced fiber orientations should not be used because of the substantially lower strengths which result. Note that all the fiber orientations are symmetric with respect to the middle plane but unbalanced in the laminate plane.

In Examples 33–36, it was desired to observe whether a laminate containing just slightly unbalanced fiber orientations toward the off-axis load ($P_z$ in FIG. 22) would result in stronger stems. The optimal fiber orientation of Example 2 was used with slightly unbalanced sheets included. Quite surprisingly, the strength of stems of this general fiber orientation was calculated to be generally reduced by the unbalanced fibers, rather than increased.

Examples 37–53 demonstrate the dramatic reduction in strength when flat plates stacked transversely to the stacking direction of the curved plies in Examples 1–36 are used. While certain lay ups can give relatively higher strengths than others (e.g. Examples 44 and 47), the position of each prepreg in the laminate has a very profound effect on strength as seen in Examples 49–53. This significant variation presents a potential danger in practical applications because of the possibility of, for example, improperly cutting or machining the blocks of laminated prepregs during the manufacture of the prosthesis.

By comparing Examples 1–36 with 37–53, it is readily apparent that the strength of stems made from longitudinally curved prepregs generally substantially exceeds that of prepregs in the shape of flat plates. Note that the optimal LCB strength of Example 2 is about 40% greater than the optimal FP strength of Example 47.

The foregoing description of the invention is illustrative and explanatory thereof. Various changes in the materials, apparatus, and particular fabrication steps employed will occur to those skilled in the art. It is intended that all such variations within the scope and spirit of the appended claims be embraced thereby.

We claim:

1. An orthopaedic device, for human implantation having improved axial bending and torque bearing properties, said device comprising:
   a curved elongated body having an outer surface and a longitudinal axis, the body comprising a matrix of biocompatible polymeric material defining the shape of the body; and
   reinforcing plies embedded within said matrix, said plies being curved in approximate correspondence with the curvature of the device and said plies being formed from fibers, said fibers being continuous and generally parallel to each other within each ply;
   wherein a majority of the plies are oriented at a non-zero angle to the longitudinal axis of the curved elongated body.

2. The device of claim 1, wherein the matrix material is selected from the group consisting of: polysulfone, polyethersulfone, polyarylsulfone, polyphenylene sulfide, polycarbonate, aromatic polyamide, aromatic polyamideimide, thermoplastic polyimide, polyaryletherketone, polyetheretherketone, polyarylethernitrile, aromatic polyhydroxyether, thermosetting phenolics and medical grade epoxies.

3. The device of claim 1, wherein the fibers are selected from the group consisting of carbon fiber, glass fiber, polyolefin fiber, polyetheretherketone fiber and polyethylene terephthalate fiber.

4. The device of claim 1, wherein said matrix material is bioresorbable.

5. The device of claim 1, wherein the fibers are bioresorbable.

6. The device of claim 1 further comprising a biocompatible coating over at least a portion of the surface of the device.

7. The device of claim 6 wherein the coating comprises a radio-opaque composition, osteo-conductive composition or a medicament.

8. The device of claim 1 further comprising:
   a sheath of continuous fibers overmolded on at least a portion of the surface of the device.

9. The device of claim 8, wherein said sheath is a mantle adapted to fit over at least a portion of the surface of the device.

10. The device of claim 1 wherein a majority of fibers are oriented at angles of between five and forty degrees.

11. The device of claim 1 wherein the plies comprise, at least in part, a first ply with fibers oriented at a first non-zero angle and a second ply, adjacent the first ply, with fibers oriented at a second non-zero angle, that is greater than the first non-zero angle.

12. The implant of claim 11 wherein the plies comprise at least three consecutive plies stacked in a sequence that includes a first ply with fibers oriented at a first non-zero angle, and a second ply with fibers oriented at a second non-zero angle that is larger than the first non-zero angle, and a third ply with fibers oriented at a third non-zero angle that is different than the first and second angles.

13. The implant of claim 11 wherein the plies comprise at least three consecutive plies stacked in a sequence that includes a first ply with fibers oriented at a first non-zero angle, a second ply with fibers oriented at a second non-zero angle that is greater than the first angle, and a third ply having fibers oriented at a non-zero angle and wherein the third ply fibers are oriented in a negative direction relative to the longitudinal axis.

14. The implant of claim 11 wherein a majority of the fibers are oriented at angles of between five and forty degrees.

15. A composite hip joint for human implantation, comprising:
   a) a stem including a distal end, a longitudinal curved body extending from the distal end, said curved body culminating in a neck;
   b) said composite hip joint having an outer surface and comprising a biocompatible polymer matrix; and
   c) reinforcing plies stacked one atop the other with the matrix, said plies being formed of continuous fibers generally parallel to each other, each of the plies being curved to substantially correspond to the longitudinal curvature of the body;
   wherein a majority of the reinforcing plies are oriented at a non-zero angle to a longitudinal axis of the longitudinal curved body of the hip joint stem.

16. The hip joint of claim 15, wherein the matrix material is selected from the group consisting of: polysulfone, polyethersulfone, polyarylsulfone, polyphenylene sulfide, polycarbonate, aromatic polyamide, aromatic polyamideimide, thermoplastic polyimide, polyaryletherketone, polyetheretherketone, polyarylethernitrile, aromatic polyhydroxyether, thermosetting phenolics and medical grade epoxies.

17. The hip joint of claim 15, wherein the fibers are selected from the group consisting of carbon fiber, glass fiber, polyolefin fiber, polyetheretherketone fiber and polyethylene terephthalate fiber.

18. The hip joint of claim 15, further comprising a sheath of continuous fibers overmolded on at least a portion of the surface of the hip joint.

19. The hip joint of claim 18 wherein the sheath is a mantle adapted to fit over at least a portion of the surface of the hip joint.

20. The hip joint of claim 15 further comprising a coating over at least a portion of the surface of the hip joint.

21. The hip joint of claim 20 wherein the coating comprises a biocompatible polymer.

22. The hip joint of claim 20 wherein the coating further comprises a radio-opaque composition, an osteo-conductive composition or a medicament.

23. An orthopaedic device having improved axial, bending and torque bearing properties for human implantation; comprising:
   a body with a longitudinal curve and a longitudinal axis;
   a matrix of biocompatible polymeric material defining the shape of the body and having an outer surface; and
   a plurality of planar reinforcing fiber plies embedded within said matrix, said plies each having a longitudinal axis;
   wherein the fibers with each ply are continuous and oriented parallel to the longitudinal axis of each ply and a majority of the planar plies are oriented at a non-zero angle to the longitudinal axis of the device.

24. The device of claim 23 wherein the fibers in consecutive plies are stacked in a sequence $(0_2/\pm7.5/\pm15/\pm22.5/\pm30)s$ relative to the longitudinal axis of the device.

25. The device of claim 23 wherein the fibers in consecutive plies are stacked in a sequent $(-20, -25, -65)_s$ relative to the longitudinal axis of the device.

26. The device of claim 23 wherein said fibers are selected from the group consisting of carbon, glass fiber, polyolefin fiber, polyetheretherketone fiber and polyethylene terephthalate fiber.

27. The device of claim 23 wherein said matrix material is bioresorbable.

28. The device of claim 23 wherein said fibers are bioresorbable.

29. The device of claim 23 further comprising a bioresorbable coating over at least a portion of the surface of the device.

30. The device of claim 29 wherein the coating comprises a biocompatible polymer.

31. The device of claim 30 wherein said coating is selected from the group consisting of polysulfone, polyethersulfone, polyarylsulfone, polyphenylene sulfide, polycarbonate, aromatic polyamide, aromatic polyamideimide, thermoplastic polyimide, polyaryletherketone, polyetheretherketone, polyarylethernitrile, aromatic polyhydroxyether, thermosetting phenolics and medical grade epoxies.

32. The device of claim 30 wherein the coating further comprises a radio-opaque composition, osteo-conductive compositions or a medicament.

33. The device of claim 23 further comprising a sheath of continuous fibers overmolded on at least a portion of the outer surface of the device.

34. The device of claim 33 wherein said sheath is a mantle adapted to fit over at least a portion of the outer surface of the device.

35. The device of claim 23, wherein the matrix material is selected from the group consisting of: polysulfone, polyethersulfone, polyarylsulfone, polyphenylene sulfide, polycarbonate, aromatic polyamide, aromatic polyamideimide, thermoplastic polyimide, polyaryletherketone, polyetheretherketone, polyarylethernitrile, aromatic polyhydroxyether, thermosetting phenolics and medical grade epoxies.

36. The device of claim 23 wherein the fibers are selected from the group consisting of carbon fiber, glass fiber, polyolefin fiber, polyetheretherketone fiber and polyethylene terephthalate fiber.

37. A composite hip joint for human implantation comprising a stem with a distal end, a longitudinal curved body with a longitudinal axis, a neck, and an outer surface, the hip joint comprising:
   a longitudinally curved biocompatible polymer matrix; and
   reinforcing planar plies embedded in the matrix, said plies being formed of continuous fibers generally parallel to each other;
   wherein a majority of the planar plies are oriented at a non-zero angle to the longitudinal axis.

38. The devices of claim 37 wherein the fibers in consecutive plies are stacked in a sequence $(0_2\pm7.5/\pm15/\pm22.5/\pm30)s$ relative to the longitudinal axis of the device.

39. The device of claim 37 wherein the fibers in consecutive plies are stacked in a sequence $(-20, -25, \pm65)_s$ relative to the longitudinal axis of the device.

40. The device of claim 37 wherein said fibers are selected from the group consisting of carbon, glass fiber, polyolefin fiber, polyetheretherketone fiber and polyethylene terephthalate fiber.

41. The device of claim 37 wherein said matrix material is bioresorbable.

42. The device of claim 37 wherein said fibers are bioresorbable.

43. The device of claim 37 further comprising a bioresorbable coating over at least a portion of the outer surface of the device.

44. The device of claim 43 wherein the coating comprises a biocompatible polymer.

45. The device of claim 44 wherein said coating is selected from the group consisting of polysulfone, polyethersulfone, polyarylsulfone, polyphenylene sulfide, polycarbonate, aromatic polyamide, aromatic polyamideimide, thermoplastic polyimide, polyaryletherketone, polyetheretherketone, polyarylethernitrile, aromatic polyhydroxyether, thermosetting phenholics and medical grade epoxies.

46. The device of claim 44 wherein the coating further comprises a radio-opaque composition, osteo-conductive compositions or a medicament.

47. The device of claim 37 further comprising a sheath of continuous fibers overmolded on at least a portion of the surface of the device.

48. The device of claim 47, wherein said sheath is a mantle adapted to fit over at least a portion of the surface of the device.

49. The implant of claim 15 wherein the non-zero angle is at least five degrees.

50. The implant of claim 49 wherein the non-zero angle is between five and forty degrees.

51. The implant of claim 15 wherein the plies comprise, at least in part, a first ply with fibers oriented at a first non-zero angle and a second ply adjacent the first play with fibers oriented at a second non-zero angle that is greater than the first non-zero angle.

52. The implant of claim 51 wherein the plies comprise at least three consecutive plies stacked in a sequence that includes a first ply with fibers oriented at a first non-zero angle, and a second ply with fibers oriented at a second non-zero angle that is larger than the first non-zero angle, and a third ply with fibers oriented at a third non-zero angle that is different than the first and second angles.

53. The implant of claim 51 wherein the plies comprise at least three consecutive plies stacked in a sequence that includes a first ply with fibers oriented at a first non-zero angle, a second ply with fibers oriented at a second non-zero angle that is greater than the first angle, and a third ply having fibers oriented at a non-zero angle and wherein the third ply fibers are oriented in a negative direction relative to the longitudinal axis.

54. The implant of claim 51 wherein a majority of the fibers are oriented at angles of between five and forty degrees.

55. The implant of claim 52 wherein a majority of fibers are oriented at angles of between five and forty degrees.

56. An orthopedic prosthetic device having improved axial, bending and torque bearing properties, said device comprising:
   an elongated prosthesis body formed of a laminated composite having a longitudinal axis;
   the laminated composite having an outer surface and being formed of plies, each ply comprising reinforcing fibers imbedded in a matrix of biocompatible polymeric material, the fibers in each ply being generally parallel to each other, the plies being fused together to form said laminate composite;
   wherein at least a majority of the plies are oriented at a non-zero angle relative to the longitudinal axis of the prosthetic device.

57. The device of claim 56 wherein a majority of fibers are oriented at angles of between five and forty degrees.

58. The device of claim 56 wherein the fibers in consecutive plies are stacked in a sequence $(0_2/\pm7.5/\pm15/\pm22.5\pm30)_s$ relative to the longitudinal axis of the device.

59. The device of claim 56 wherein the fibers in consecutive plies are stacked in a sequence $(0_2/(\pm20)_4)_s$ relative to the longitudinal axis of the device.

60. The device of 56 wherein the fibers in consecutive plies are stacked in a sequence $(0_2/\pm20/\pm30/\pm20/\pm30)_s$ relative to the longitudinal axis of the device.

61. The device of claim 56 wherein the biocompatible polymeric material is selected from the group consisting of polysulfone, polyethersulfone, polyarylsulfone, polyphenylene sulfide, polycarbonate, aromatic polyamide, aromatic polyamideimide, thermoplastic polyimide, polyaryletherketone, polyetheretherketone, polyarylethernitrile, aromatic polyhydroxyether, thermosetting phenolics and medical grade epoxies.

62. The device of claim 61 wherein the fibers are selected from the group consisting of carbon fiber, glass fiber, polyolefin fiber, polyetheretherketone fiber and polyethylene fiber.

63. The device of claim 62 further comprising a biocompatible coating over at least a portion of the outer surface of the laminate composite.

64. The device of claim 63 wherein the coating comprises a radio-opaque composition, osteo-conductive compositions, or a medicament.

65. The device of claim 56 further comprising a sheath of continuous fibers over molded on at least a portion of the outer surface of the laminated composite.

66. The device of claim 65 wherein the sheath is a mantle adapted to cover at least a portion of the outer surface of the laminated composite.

* * * * *